(12) United States Patent
Mills et al.

(10) Patent No.: US 6,839,496 B1
(45) Date of Patent: Jan. 4, 2005

(54) OPTICAL FIBRE PROBE FOR PHOTOACOUSTIC MATERIAL ANALYSIS

(75) Inventors: Timothy Noel Mills, London (GB); Paul Beard, London (GB); David Delpy, London (GB)

(73) Assignee: University College of London, London (GB)

( * ) Notice: Subject to any disclaimer, the term of this patent is extended or adjusted under 35 U.S.C. 154(b) by 255 days.

(21) Appl. No.: 10/019,741

(22) PCT Filed: Jun. 23, 2000

(86) PCT No.: PCT/GB00/02491
§ 371 (c)(1),
(2), (4) Date: May 2, 2002

(87) PCT Pub. No.: WO01/01111
PCT Pub. Date: Jan. 4, 2001

(30) Foreign Application Priority Data

Jun. 28, 1999 (GB) .............................. 9915082

(51) Int. Cl.[7] .............................. G02B 6/02; G02B 6/06
(52) U.S. Cl. ........................ 385/126; 385/117; 385/116
(58) Field of Search ................................ 385/126–128, 385/38, 116, 117; 600/476, 478; 356/502, 477, 432

(56) References Cited

U.S. PATENT DOCUMENTS

| | | | |
|---|---|---|---|
| 4,567,769 A | | 2/1986 | Barkhoudarian |
| 5,125,749 A | * | 6/1992 | Leugers et al. .............. 356/432 |
| 5,348,002 A | * | 9/1994 | Caro ............................ 600/310 |
| 5,718,231 A | * | 2/1998 | Dewhurst et al. ............ 600/462 |
| 5,840,023 A | * | 11/1998 | Oraevsky et al. ............ 600/407 |
| 6,403,944 B1 | * | 6/2002 | MacKenzie et al. ........... 356/41 |
| 6,498,942 B1 | * | 12/2002 | Esenaliev et al. ............ 600/310 |

FOREIGN PATENT DOCUMENTS

| | | |
|---|---|---|
| GB | 2294323 A | 4/1996 |
| GB | 2322941 A | 9/1998 |
| WO | WO 97/27801 A1 | 8/1997 |

OTHER PUBLICATIONS

Beard "Optical Fiber Photacoustic—Photothermal Probe", Optics Letters, vol. 23, No. 15, Aug. 1, 1998, pp1235–1237.
British Search Report of Sep. 16, 1999.
Beard "Characterization of post mortem arterial tissue using time–resolved spectroscopy at 436, 461 and 532 nm", Phys. Med. Biol. vol. 42, 1997, pp177–198.
Rao, "Prototype fiber–optic–based Fizeau medical pressure sensor that uses coherence reading", Optics Letters, vol. 18, No. 24, Dec. 15, 1993, pp 2153–2155.

* cited by examiner

*Primary Examiner*—Joseph Williams
*Assistant Examiner*—Peter Macchiarolo
(74) *Attorney, Agent, or Firm*—Barnes & Thornburg LLP

(57) ABSTRACT

A probe comprises an excitation source and a double-core optical fiber. A pulsed laser signal (20) of the excitation sources supplied to the outer core (42) at one end of the optical fiber. The other end is provided with an interferometer film (18). An excitation signal (22) produced in the sample (10) modulates the thickness of the film (18). This provides an interferometer signal (26, 28) detected from the inner core (40).

6 Claims, 1 Drawing Sheet

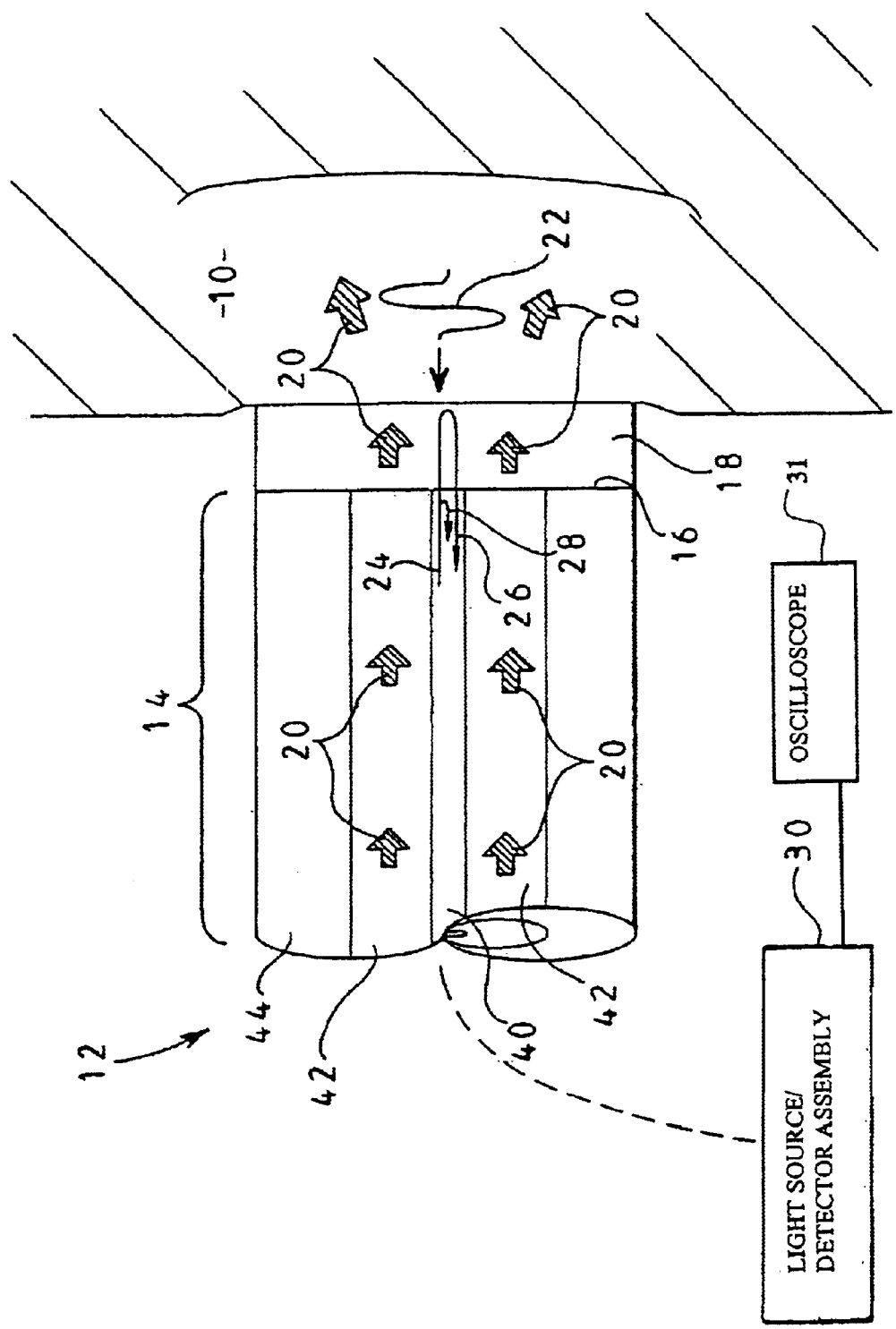

OPTICAL FIBRE PROBE FOR PHOTOACOUSTIC MATERIAL ANALYSIS

This invention relates to optical fibre probes for the excitation of a sample to produce signals for analysis. These signals may comprise photoacoustic and/or photothermal waves.

Such probes have been proposed for characterising arterial tissue prior to treatment of narrowed blood vessels, for example caused by atheroma. Pulsed laser signals have been proposed as the excitation signal, which result in the generation of an acoustic signal through thermal expansion effects within the sample. Excitation signals of different wavelengths have been proposed in order to generate a photoacoustic signature which conveys different types of information concerning the sample.

For example, it has been found that the photoacoustic signals generated by laser excitation of wavelength around 450 nm (e.g. 436 and 461 nm) may be analysed to detect the presence of atheroma, based on the different attenuations of the excitation signal in the atheroma and in normal tissue. Alternatively, an excitation signal of longer wavelength, for example 530 nm, may be employed to enable thickness measurement of the sample. At this wavelength, the excitation signal penetrates through the sample, and timing analysis of the signals generated at the boundaries of tissue layers enables a thickness calculation to be performed.

Analysis of arterial tissue using pulsed laser excitation to generate acoustic and thermal signals is discussed in detail in the article "Characterization of post mortem arterial tissue using time-resolved photoacoustic spectroscopy at 436, 461 and 532 nm" in Phys. Med. Biol. 42 (1997) pages 177–19.

A design of optical fibre probe suitable for sample analysis as described above is disclosed in the article "Optical fiber photoacoustic-photothermal probe" published in Optics Letters Vol. 23, No. 15 of 1 Aug. 1998. The probe comprises a multimode optical fibre with a transparent Fabry-Perot polymer film sensor mounted at its distal end, which is placed in contact with the sample for analysis. Optical pulses are launched into the fibre and absorbed in the target resulting in the generation of ultrasonic thermoelastic waves for detection by the sensor.

A problem with the probe design described above is that the wavelength of the generated acoustic signal may be small compared to the diameter of the sensing region which is defined by the core diameter of the multimode fibre. As a result, the interferometer may not detect signals with oblique entry angles, for example edge wave signals that arise due to diffraction effects.

According to the invention, there is provided a probe for the excitation of a sample to produce an acoustic signal and for analysis of the signal, comprising:
  an excitation source which provides a pulsed laser output;
  an optical fibre having a central inner core, a concentric outer core and an outer cladding, the pulsed laser output being supplied to the outer core at a first end of the optical fibre, the second end of the optical fibre being provided with an interferometer film which is substantially transparent to the laser pulses, a signal produced in the sample modulating the thickness of the film; and
  a light source and detector assembly which provides an interferometer signal to the inner core at the first end of the fibre and detects the modulated reflected signal received from the inner core.

The probe of the invention has a small inner core which acts as the sensing part of the probe, but has a larger concentric outer core for carrying the laser excitation pulses. The probe is therefore able to carry the required energy signal for excitation of the sample, but also provides a small sensing area defined by the central inner core. This increases the frequency range of signals which can be detected at non-normal angles of incidence. Accordingly the sensitivity of the device is increased to changes in the temporal characteristics of the signal. The signal may comprise an acoustic wave or thermal wave.

Preferably, the inner core is a single mode fibre, which may have a diameter of less than 10 $\mu$m and preferably around 6 $\mu$m. This may result in an analysis probe having an active area of less than 10 $\mu$m. This enables the analysis function of the probe to be responsive to plane wave components and edge wave components of the generated acoustic signal.

One possible use of the probe is in medical examination equipment for characterising biological tissue, for example arterial tissue.

The invention will now be described by way of example, with reference to and as shown in the accompanying drawing which shows a probe of the invention in use for analysing a sample.

The FIGURE shows a sample 10 for analysis using the probe 12 of the invention. The probe 12 comprises an optical fibre 14 having a cleaved and polished end face 16 against which a polymer interferometer film 18 is provided. The polymer film 18 is transparent so that laser excitation pulses, represented schematically as arrows 20 in the FIGURE, may be introduced into the sample 10 through the film 18. These pulses 20 may comprise nanosecond, submillijoule optical pulses which are absorbed in the biological sample 10, thereby producing thermal waves with a typical duration of the order of a few hundred milliseconds. Rapid thermal expansion occurs within the sample 10 generating ultrasonic thermoelastic waves with a typical duration of several hundred nanoseconds. The thermoelastic waves comprise an acoustic signal 22 which modulates the thickness of the film 18. Of course, other excitation signals may be used, depending upon the nature of the sample under analysis.

The interferometer defined by the film 18 is illuminated by light launched into the fibre from a continuous wave low-power laser source. The acoustic wave 22 modulates the thickness of the film 18 and hence the optical phase difference between the reflections from the two sides of the film. Similarly, the thermal waves modulate the optical thickness of the film which is also detectable as a result of the optical phase differences. In each case, a corresponding intensity modulation in the light reflected from the sensing film is produced, which is then detected. The reflections take place at the two faces of the film 18, as a result of the refractive index mismatch at the two sides of the film. Wavelength-selective dielectric reflective coatings may be applied to the faces of the film 18, which are transparent to the excitation pulses but reflective to the wavelength of the continuous wave signal. Shown schematically in the FIGURE is an incident light signal 24 and the two reflected signals 26, 28.

The laser excitation pulses 20 are produced by a frequency-doubled Q-switched Nd:YAG laser operating at 532 nm or by a tuneable dye laser. The laser forms part of an excitation source and light source/detector assembly 30, which also provides the continuous wave output for interrogation of the interferometer. This continuous wave output may be derived from a tuneable continuous wave source such as a laser diode.

The excitation pulses 20 may have a wavelength which is selected in dependence upon the desired characteristic of the sample 10 to be analysed and upon the nature of the sample.

For example, the pulses may have a wavelength which is such that they penetrate the entire thickness of the sample 10. In this case thermoelastic waves will be generated at the two surfaces of the sample 10, and the detector assembly may then enable the thickness of the sample to be calculated. Alternatively, an excitation wavelength could be chosen to generate different thermoelastic signals depending upon the attenuation characteristics of the sample 10, which may enable an operator to distinguish between normal and abnormal biological tissue, for example normal and abnormal arterial tissue.

The detector assembly of the unit 30 may comprise a silicon pin photodiode, the output of which is preferably displayed on an oscilloscope.

To the extent described above, the construction of the probe is known. In accordance with the invention, the optical fibre 14 comprises a central inner core 40, a concentric outer core 42 and an outer cladding 44. Such double-core concentric fibres are known for use in other applications, such as optical fibre lasers and laser amplifiers. The method of constructing such a fibre will not therefore be described. The pulsed laser output 20 is supplied to the outer core 42 by the unit 30, whereas the interrogation signal 24 is provided by the unit 30 to the inner core 40. The modulated reflected signal provided by the interferometer film 18 is transmitted down the inner core 40 to the detector part of the unit 30.

The spot size of the interrogating continuous wave source is focused to match the core diameter of the inner fibre, and the spot size of the excitation pulses matches the outer fibre diameter. Some energy from the excitation pulses will travel down the central core, but the selection of different wavelengths for the excitation signal and the interrogation signal will enable the detector 30 to distinguish between those signals using spectral analysis.

Conventional apparatus may be employed to launch the excitation and interrogation signals into the fibre, for example using half-silvered mirrors to combine the signals from the two sources.

The inner core 40 preferably defines a single mode fibre, with the outer core 42 acting as cladding of the inner core. For this purpose, the inner core 40 has a higher refractive index than the outer core 42. The outer core 42 is capable of carrying higher energy signals, and the surrounding cladding 44 has a lower refractive index than the outer core 42.

The inner core 40 preferably has a diameter of 5–10 $\mu$m, whereas the outer core has a diameter of approximately 250 $\mu$m.

The use of a physically small, and preferably single mode, inner core as the transport medium for the interferometer signals enables the sensing device to have a small active area. This enables the device to detect input signals of a wide range of wavelengths at non-normal angles of incidence. Input signals entering the sensor at an angle to the longitudinal axis of the sensor will be integrated over the active area of the sensor, and as a result a smaller active area improves the directional characteristics of the sensor. The excitation signal causes the sample to produce plane wave and edge wave components. The edge wave component is a rarefaction wave generated at the outside edge of the envelope of the excitation signal. The edge wave and plane wave components carry different information concerning the sample being analysed. The probe of the invention enables the edge wave components, which enter the probe at an oblique angle, to be detected due to the small active area which reduces band limiting of the probe response. The edge wave components will always enter the probe at an oblique angle, irrespective of the direction faced by the probe, as they result from the edge of the excitation signal produced by the probe.

Furthermore, the physical spacing between the outside of the outer core and the inner core enables the probe to separate the plane wave and edge wave signals from the combined signal received by the probe. This separation may be achieved by temporal analysis.

The acoustic signals 22 produced in the sample 10 may typically have frequencies up to 30 MHz, and for acoustic signals travelling in fresh water this corresponds to a wavelength of 47 $\mu$m. Preferably, therefore, the active area of the sensor is less than 20 $\mu$m, so that the sensor can be responsive to 30 MHz acoustic signals. The detection bandwidth then exceeds the range of frequencies of the input signal, the sensor having omnidirectional response.

A single mode fibre is not able to carry the required Q-switched laser pulses for the excitation of the sample, and these are provided in the outer core 42. The larger area of the outer core 42 enables an excitation wave to be introduced into the sample 10 over a much greater area than the sensor area defined by the central inner core 40.

The small active area of the interferometer also facilitates the production of a polymer film 18 having extremely parallel and uniform opposite faces over the area of interest of the sensor. The sensing film may comprise a disc of PET (polyethylene terepthalate). Such discs may be cut from a larger film, and the smaller the required area the more uniform will be the film thickness.

The design of the excitation source and light source/detector assembly 30 will be apparent to those skilled in the art, and specific examples have been given above. Thus, the light source may comprise a tuneable laser diode which may produce light of around 850 nm, and it may be tuned to obtain quadrature operation of the interferometer. The detector assembly may comprise a photodiode, as discussed above, and may have an integral transimpedance amplifier.

There are various possible applications in which the probe of the invention may be used, in addition to the analysis of biological tissue. Such applications may include medical as well as non-medical sample analysis.

What is claimed is:

1. A probe for the excitation of a sample to produce an acoustic signal and for analysis of the signal, comprising:
   an excitation source which provides a pulsed laser output;
   an optical fibre having a central inner core, a concentric outer core and an outer cladding, the pulsed laser output being supplied to the outer core at a first end of the optical fibre, the second end of the optical fibre being provided with an interferometer film which is substantially transparent to the laser pulses, said acoustic signal produced in the sample modulating the thickness of the film; and
   a light source and detector assembly which provides an interferometer signal to the inner core at the first end of the fibre and detects the modulated reflected signal received from the inner core.

2. A probe as claimed in claim 1, wherein the inner core is a single mode fibre.

3. A probe as claimed in claim 2, wherein the diameter of the inner core is less than 10 $\mu$m.

4. A probe as claimed in claim 1, wherein the outer diameter of the outer core is approximately 250 $\mu$m.

5. A probe as claimed in claim 1, wherein the interferometer film is butted against the second end of the fibre.

6. Medical examination equipment for characterising biological tissue comprising a probe as claimed in claim 1 and means for displaying the detected modulated reflected signal.

* * * * *